United States Patent
Kubanek et al.

(10) Patent No.: US 8,765,634 B2
(45) Date of Patent: Jul. 1, 2014

(54) PROCESSES FOR PREPARING AMINES AND ZIRCONIUM DIOXIDE- AND NICKEL-CONTAINING CATALYSTS FOR USE THEREIN

(75) Inventors: Petr Kubanek, Mannheim (DE); Bram Willem Hoffer, Heidelberg (DE); Ekkehard Schwab, Neustadt (DE); Johann-Peter Melder, Böhl-Iggelheim (DE); Holger Evers, München (DE); Till Gerlach, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/271,038

(22) Filed: Oct. 11, 2011

(65) Prior Publication Data

US 2012/0035049 A1 Feb. 9, 2012

Related U.S. Application Data

(62) Division of application No. 12/373,825, filed as application No. PCT/EP2007/056725 on Jul. 4, 2007, now Pat. No. 8,063,252.

(30) Foreign Application Priority Data

Jul. 14, 2006 (EP) .................................... 06117249

(51) Int. Cl.
*B01J 23/00* (2006.01)

(52) U.S. Cl.
USPC ........... 502/350; 502/308; 502/313; 502/317; 502/319; 564/471; 564/478; 564/469; 564/511

(58) Field of Classification Search
None
See application file for complete search history.

(56) References Cited

U.S. PATENT DOCUMENTS

| | | | |
|---|---|---|---|
| 3,275,554 A | 9/1966 | Wagenaar | |
| 3,751,475 A | 8/1973 | van der Voort et al. | |
| 3,922,303 A | 11/1975 | Takehara et al. | |
| 4,152,353 A | 5/1979 | Habermann | |
| 4,153,581 A | 5/1979 | Habermann | |
| 4,625,030 A | 11/1986 | Best | |
| 4,832,702 A | 5/1989 | Kummer et al. | |
| 5,002,922 A | 3/1991 | Irgang et al. | |
| 5,530,127 A | 6/1996 | Reif et al. | |
| 5,608,113 A | 3/1997 | Becker et al. | |
| 5,958,825 A | 9/1999 | Wulff-Doring et al. | |
| 6,057,442 A | 5/2000 | Wulff-Döring et al. | |
| 6,417,353 B1 | 7/2002 | Funke et al. | |
| 6,525,222 B2 | 2/2003 | Nouwen et al. | |
| 6,821,396 B2 | 11/2004 | Wolfert et al. | |
| 6,986,833 B2 | 1/2006 | Wölfert et al. | |
| 7,034,186 B2 | 4/2006 | Gerlach et al. | |
| 7,183,438 B2 | 2/2007 | Gerlach et al. | |
| 7,196,033 B2 | 3/2007 | Renken et al. | |
| 7,750,189 B2 | 7/2010 | Kubanek et al. | |
| 7,754,922 B2 | 7/2010 | Kubanek et al. | |
| 7,919,655 B2 | 4/2011 | Kubanek et al. | |
| 2003/0139289 A1* | 7/2003 | Renken et al. ................. | 502/308 |
| 2005/0107637 A1* | 5/2005 | Gerlach et al. ................ | 564/471 |
| 2005/0154235 A1* | 7/2005 | Bohling et al. ............... | 564/469 |
| 2008/0146846 A1 | 6/2008 | Dialer et al. | |
| 2008/0255351 A1 | 10/2008 | Hoffer et al. | |
| 2009/0264652 A1 | 10/2009 | Kubanek et al. | |
| 2009/0275781 A1 | 11/2009 | Kubanek et al. | |
| 2009/0286977 A1 | 11/2009 | Kubanek et al. | |
| 2009/0312579 A1 | 12/2009 | Kubanek et al. | |
| 2010/0010264 A1 | 1/2010 | Kubanek et al. | |
| 2010/0267948 A1 | 10/2010 | Eberhardt et al. | |
| 2010/0274010 A1 | 10/2010 | Kubanek et al. | |
| 2010/0274011 A1 | 10/2010 | Kubanek et al. | |
| 2010/0274055 A1 | 10/2010 | Kubanek et al. | |
| 2011/0054167 A1 | 3/2011 | Kubanek et al. | |

FOREIGN PATENT DOCUMENTS

| | | |
|---|---|---|
| DE | 2125039 | 12/1971 |
| DE | 3611230 A1 | 10/1987 |
| DE | 102004062253 A1 | 7/2006 |
| EP | 0382049 A1 | 8/1990 |
| EP | 0514692 A2 | 11/1992 |
| EP | 0696572 A1 | 2/1996 |
| EP | 0697395 A2 | 2/1996 |
| EP | 729785 A1 | 9/1996 |
| EP | 0839575 | 5/1998 |
| EP | 0878462 A1 | 11/1998 |
| EP | 0905122 A2 | 3/1999 |
| EP | 0963975 A1 | 12/1999 |
| EP | 1035106 A1 | 9/2000 |
| EP | 1106600 A2 | 6/2001 |
| EP | 1312599 A1 | 5/2003 |
| EP | 1312600 A1 | 5/2003 |
| EP | 1431271 A1 | 6/2004 |
| JP | 7185346 A | 7/1995 |
| WO | WO-00/69804 A1 | 11/2000 |

(Continued)

OTHER PUBLICATIONS

Translation of the Notification of Reasons for Refusal of Japan Patent Application No. 2009-519905.

*Primary Examiner* — Melvin C Mayes
*Assistant Examiner* — Colette Nguyen
(74) *Attorney, Agent, or Firm* — Novak Druce Connolly Bove + Quigg LLP

(57) ABSTRACT

A catalytically active composition comprising, prior to reduction with hydrogen: 10 to 75% by weight of an oxygen compound of zirconium, calculated as $ZrO_2$; 1 to 30% by weight of an oxygen compound of copper, calculated as CuO; 10 to 50% by weight of an oxygen compound of nickel, calculated as NiO; 10 to 50% by weight of an oxygen compound of cobalt, calculated as CoO; and 0.1 to 10% by weight of one or more oxygen compounds of one or more metals selected from the group consisting of Pb, Bi, Sn, Sb and In, calculated as PbO, $Bi_2O_3$, SnO, $Sb_2O_3$ or $In_2O_3$, respectively.

6 Claims, No Drawings

(56) References Cited

FOREIGN PATENT DOCUMENTS

| WO | WO-03/051508 A1 | 6/2003 |
| WO | WO-03/076386 A2 | 9/2003 |
| WO | WO-2006/069673 A1 | 7/2006 |
| WO | WO-2007/036496 A1 | 4/2007 |
| WO | WO-2008/006748 A1 | 1/2008 |
| WO | WO-2008/006749 A1 | 1/2008 |
| WO | WO-2008/006750 A1 | 1/2008 |
| WO | WO-2008/006752 A1 | 1/2008 |
| WO | WO-2008/006754 A1 | 1/2008 |

* cited by examiner

PROCESSES FOR PREPARING AMINES AND ZIRCONIUM DIOXIDE- AND NICKEL-CONTAINING CATALYSTS FOR USE THEREIN

CROSS-REFERENCE TO RELATED APPLICATIONS

This application is a divisional application, under 35 U.S.C. §121, of U.S. patent application Ser. No. 12/373,825, filed Jan. 14, 2009, now U.S. Pat. No. 8,063,252, which is a national stage application, under 35 U.S.C. §371, of PCT/EP2007/056725 filed Jul. 4, 2007, which claims benefit of European Patent Application No. 06117249.0 filed Jul. 14, 2006. The entire contents of each of the foregoing applications are incorporated herein by reference in their entireties.

FIELD OF THE INVENTION

The present invention relates to catalysts comprising zirconium dioxide and nickel and a process for preparing an amine by reaction of a primary or secondary alcohol, aldehyde and/or ketone with hydrogen and a nitrogen compound selected from the group consisting of ammonia, primary and secondary amines in the presence of a catalyst comprising zirconium dioxide and nickel.

BACKGROUND

The process products are used, inter alia, as intermediates in the production of fuel additives (U.S. Pat. No. 3,275,554; DE-A-21 25 039 and DE-A-36 11 230), surfactants, drugs and crop protection agents, hardeners for epoxy resins, catalysts for polyurethanes, intermediates for the preparation of quaternary ammonium compounds, plasticizers, corrosion inhibitors, synthetic resins, ion exchangers, textile assistants, dyes, vulcanization accelerators and/or emulsifiers.

U.S. Pat. No. 4,153,581 (Habermann) relates to amination of alcohols, aldehydes or ketones by means of specific Co/Cu catalysts comprising Fe, Zn and/or Zr.

U.S. Pat. No. 4,152,353 (Dow) relates to amination of alcohols, aldehydes or ketones by means of specific Ni/Cu catalysts comprising Fe, Zn and/or Zr.

EP-A1-382 049 (BASF AG) discloses catalysts which comprise oxygen-comprising zirconium, copper, cobalt and nickel compounds and processes for the hydrogenative amination of alcohols. The preferred zirconium oxide content of these catalysts is from 70 to 80% by weight (loc. cit.: page 2, last paragraph; page 3, 3rd paragraph; examples). Although these catalysts have a good activity and selectivity, they display operating lives which are in need of improvement.

EP-A2-514 692 (BASF AG) discloses catalysts comprising copper oxide, nickel oxide and/or cobalt oxide, zirconium oxide and/or aluminum oxide for the catalytic amination of alcohols by means of ammonia or primary amines and hydrogen in the gas phase. This patent application teaches that in these catalysts the atomic ratio of nickel to copper has to be from 0.1 to 1.0, preferably from 0.2 to 0.5 (a loc. cit.: example 1), since otherwise there is increased formation of yield-reducing by-products in the amination of alcohols (loc. cit.: examples 6 and 12). Aluminum oxide is preferably used as support (loc. cit.: examples 1 to 5 and 7 to 11).

EP-A1-696 572 and EP-A-697 395 (both BASF AG) disclose catalysts comprising nickel oxide, copper oxide, zirconium oxide and molybdenum oxide for the catalytic amination of alcohols by means of nitrogen compounds and hydrogen. Although high conversions are achieved using these catalysts, by-products which themselves, or after conversion into subsequent products, can interfere in the work-up can be formed.

EP-A2-905 122 (BASF AG) describes a process for preparing amines from alcohols and nitrogen compounds using a catalyst whose catalytically active composition comprises oxygen-comprising compounds of zirconium, copper and nickel and no oxygen-comprising compounds of cobalt or molybdenum.

EP-A-1 035 106 (BASF AG) relates to the use of catalysts comprising oxygen-comprising compounds of zirconium, copper and nickel for preparing amines by aminative hydrogenation of aldehydes or ketones.

EP-A1-963 975 and EP-A2-1 106 600 (both BASF AG) describe processes for preparing amines from alcohols or aldehydes or ketones and nitrogen compounds using a catalyst whose catalytically active composition comprises 22-40% by weight (or 22-45% by weight) of oxygen-comprising compounds of zirconium, 1-30% by weight of oxygen-comprising compounds of copper and 15-50% by weight (or 5-50% by weight) of oxygen-comprising compounds of each of nickel and cobalt.

WO-A-03/076386 and EP-A1-1 431 271 (both BASF AG) also teach catalysts of the abovementioned type for aminations.

WO-A1-03/051508 (Huntsman Petrochemical Corp.) relates to processes for the amination of alcohols using specific Cu/Ni/Zr/Sn-comprising catalysts which, in a further embodiment, comprise Cr instead of Zr (see page 4, lines 10-16).

The European patent application No. 06101339.7 of Feb. 6, 2006 (BASF AG) describes a process for preparing aminodiglycol (ADG) and morpholine by reaction of diethylene glycol (DEG) with ammonia in the presence of a heterogeneous transition metal catalyst, in which the catalytically active composition of the catalyst prior to treatment with hydrogen comprises oxygen-comprising compounds of aluminum and/or zirconium, copper, nickel and cobalt and the shaped catalyst body has specific dimensions.

Four parallel European patent applications having the same filing date (all BASF AG) relate to particular doped catalysts comprising zirconium dioxide, copper and nickel and their use in processes for preparing an amine by reaction of a primary or secondary alcohol, aldehyde and/or ketone with hydrogen and ammonia, a primary or secondary amine.

When the very active catalysts of the prior art, in particular the catalysts according to EP-A1-696 572, EP-A1-963 975 and EP-A2-1 106 600 (see above) are used, increased decarbonylation of the carbonyl function (possibly formed as an intermediate) of the starting materials (alcohols, aldehyde, ketone) occurs at elevated temperature. The formation of methane by hydrogenation of carbon monoxide (CO) leads, owing to the large quantity of heat of hydrogenation liberated, to a risk of a "runaway reaction", i.e. an uncontrolled temperature increase in the reactor. If CO is scavenged by amines, formation of secondary components comprising methyl groups results.

In the amination of diethylene glycol (DEG), there is, for example, increased formation of undesirable methoxyethanol or methoxyethylamine.

In the example of the amination of diethylene glycol (DEG), the "decarbonylation" is considered to be, in particular, the sum of undesirable components (methanol, methoxyethanol, methoxyethylamine, N-methylmorpholine and methoxyethyl-morpholine), which are formed from DEG by a reaction network via methoxyethanol:

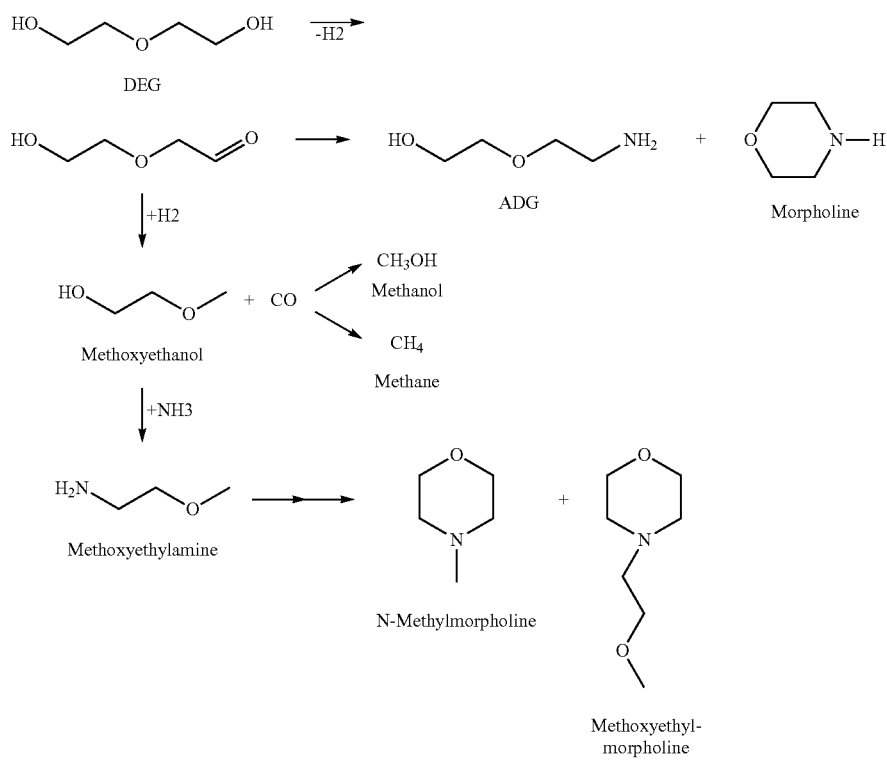

As reaction mechanism of the amination of primary or secondary alcohols, it is assumed that the alcohol is initially dehydrogenated at a metal center to form the corresponding aldehyde. The copper is presumably of particular importance as dehydrogenation component. If aldehydes are used for the amination, this step is eliminated.

The aldehyde formed or used can be aminated by reaction with ammonia or primary or secondary amine with elimination of water and subsequent hydrogenation. This condensation of the aldehyde with the abovementioned nitrogen compound is presumably catalyzed by acid sites in the catalyst. However, the aldehyde can also be decarbonylated in an undesirable secondary reaction, i.e. the aldehyde function is split off as CO. The decarbonylation or methanization presumably takes place at a metallic center. The CO is hydrogenated to methane over the hydrogenation catalyst, so that the formation of methane acts as an indicator of the extent of decarbonylation. The decarbonylation forms the abovementioned undesirable by-products such as, in the abovementioned case, methoxyethanol and/or methoxyethylamine.

The undesirable condensation of the aldehyde with ammonia or primary or secondary amine and the undesirable decarbonylation of the aldehyde are parallel reactions of which the undesirable condensation is presumably acid-catalyzed while the undesirable decarbonylation is catalyzed by metallic centers.

BRIEF SUMMARY

It is an object of the present invention to improve the economics of previous processes for the hydrogenative amination of aldehydes or ketones and the amination of alcohols and to remedy a disadvantage or a plurality of disadvantages of the prior art, in particular the abovementioned disadvantages. Catalysts which can be produced industrially in a simple manner and allow the abovementioned aminations to be carried out with high conversion, high yield, space-time yields (STYs), selectivity, catalyst operating life combined with high mechanical stability of the shaped catalyst body and a low risk of a "runaway reaction" are to be found. The catalysts should accordingly have a high activity and a high chemical and mechanical stability under the reaction conditions.

[Space-time yields are reported in "Amount of product/(catalyst volume·time)"(kg/($l_{cat.}$·h)) and/or "Amount of product/(reactor volume·time)"(kg/($l_{reactor}$·h)].

We have accordingly found a process for preparing an amine by reaction of a primary or secondary alcohol, aldehyde and/or ketone with hydrogen and a nitrogen compound selected from the group consisting of ammonia, primary and secondary amines in the presence of a catalyst comprising zirconium dioxide and nickel, wherein the catalytically active composition of the catalyst prior to reduction with hydrogen comprises
oxygen-comprising compounds of zirconium, copper, nickel and cobalt and oxygen-comprising compounds of one or more metals selected from among Pb, Bi, Sn, Sb and In.

Furthermore, we have found catalysts comprising oxygen-comprising compounds of zirconium, copper, nickel and cobalt and oxygen-comprising compounds of one or more metals selected from among Pb, Bi, Sn, Sb and In.

In particular, we have found catalysts whose catalytically active composition prior to reduction with hydrogen comprises
from 10 to 75% by weight of oxygen-comprising compounds of zirconium, calculated as $ZrO_2$,
from 1 to 30% by weight of oxygen-comprising compounds of copper, calculated as CuO, from 10 to 50% by weight of oxygen-comprising compounds of nickel, calculated as NiO, and
from 10 to 50% by weight of oxygen-comprising compounds of cobalt, calculated as CoO, and
from 0.1 to 10% by weight of oxygen-comprising compounds of one or more metals selected from among Pb, Bi, Sn, Sb and In, in each case calculated as PbO, SnO, $Sb_2O_3$ or $In_2O_3$,
and their use in the abovementioned amination process, in particular in the process for the reaction of DEG with ammonia.

According to the invention, it has been recognized that the activity of the catalyst for the amination of primary or secondary alcohols, aldehydes and/or ketones in the presence of $H_2$, e.g. the amination of diethylene glycol (DEG) by means of ammonia to form aminodiglycol and morpholine, essentially remains at least constant as a result of the additional content of Pb, Bi, Sn, Sb and/or In in the zirconium-copper-nickel-cobalt catalysts but at the same time the extent of the undesirable decarbonylation reaction is reduced and the selectivity of the amination reaction is thus increased.

The process can be carried out continuously or batchwise. Preference is given to a continuous process.

DETAILED DESCRIPTION OF THE INVENTION

For the synthesis in the gas phase, the starting materials are vaporized in a targeted manner, preferably in a circulating gas stream, and fed into the reactor in gaseous form. Suitable amines for a gas-phase synthesis are amines which, due to their boiling points and the boiling points of their starting materials, can be kept in the gas phase in the process within the process parameters. The circulating gas serves firstly to vaporize the starting materials and secondly as reactant in the amination reaction.

In the gas recycle mode, the starting materials (alcohol, aldehyde and/or ketone, hydrogen and the nitrogen compound) are vaporized in a circulating gas stream and are fed in gaseous form into the reactor.

The starting materials (alcohol, aldehyde and/or ketone, the nitrogen compound) can also be vaporized as aqueous solutions and supplied to the catalyst bed with the circulating gas stream.

Preferred reactors are tube reactors. Examples of suitable reactors with a circulating gas stream may be found in Ullmann's Encyclopedia of Industrial Chemistry, 5th Ed., Vol. 4, pages 199-238, "Fixed-Bed Reactors".

As an alternative, the reaction is advantageously carried out in a shell-and-tube reactor or in a single-stream plant.

In a single-stream plant, the tube reactor in which the reaction occurs can comprise a plurality of (e.g. two or three) individual tube reactors connected in series. Optionally, intermediate introduction of feed (comprising the starting material and/or ammonia and/or $H_2$) and/or circulating gas and/or reactor output from a downstream reactor is advantageously possible here.

The amount of circulating gas is preferably in the range from 40 to 1500 $m^3$ (at operating pressure)/[$m^3$ of catalyst (bed volume)·h], in particular in the range from 100 to 700 $m^3$ (at operating pressure)/[$m^3$ of catalyst (bed volume)·h].

The circulating gas preferably comprises at least 10% by volume, particularly preferably from 50 to 100% by volume, very particularly preferably from 80 to 100% by volume, of $H_2$.

For the synthesis in the liquid phase, suitable starting materials and products are all those which are not readily vaporizable or thermally labile. In these cases, a further advantage is that vaporization and recondensation of the amine in the process is not necessary.

In the process of the invention, the catalysts are preferably used in the form of catalysts which consist entirely of catalytically active composition and optionally a shaping aid (e.g. graphite or stearic acid) if the catalyst is to be used as shaped bodies, i.e. comprise no further catalytically active accompanying substances.

In this context, the oxidic support material zirconium dioxide ($ZrO_2$) is considered to be part of the catalytically active composition.

To use the catalysts, the catalytically active composition to be milled to powder is introduced into the reaction vessel or the catalytically active composition is installed in the reactor as shaped catalyst bodies after milling, mixing with shaping aids, shaping and heat treatment, for example as pellets, spheres, rings, extrudates (e.g. extruded rods).

The figures (in % by weight) given for the concentrations of the components of the catalyst are, unless indicated otherwise, in each case based on the catalytically active composition of the finished catalyst after its last heat treatment and before it has been reduced by means of hydrogen.

The catalytically active composition of the catalyst after its last heat treatment and before it has been reduced by means of hydrogen is defined as the sum of the masses of the catalytically active constituents and the abovementioned catalyst support materials and comprises essentially the following constituents:
Zirconium dioxide ($ZrO_2$), oxygen-comprising compounds of copper, nickel and cobalt and oxygen-comprising compounds of the metal or metals Pb, Bi, Sn, Sb and In.

The sum of the abovementioned constituents of the catalytically active composition is usually from 70 to 100% by weight, preferably from 80 to 100% by weight, particularly preferably from 90 to 100% by weight, in particular >95% by weight, very particularly preferably >98% by weight, especially >99% by weight, e.g. particularly preferably 100% by weight.

The catalytically active composition of the catalysts of the invention and the catalysts used in the process of the invention can further comprise one or more elements (oxidation state 0) or their inorganic or organic compounds selected from groups I A to VI A and I B to VII B and VIII of the Periodic Table.

Examples of such elements and their compounds are: transition metals such as Re and rhenium oxides, Mn and $MnO_2$, W and tungsten oxides, Ta and tantalum oxides, Nb or niobium oxides or niobium oxalate, V and vanadium oxides and vanadyl pyrophosphate; lanthanides such as Ce and $CeO_2$ or Pr and $Pr_2O_3$; alkali metal oxides such as $Na_2O$; alkali metal carbonates such as $Na_2CO_3$; alkaline earth metal oxides such as SrO; alkaline earth metal carbonates such as $MgCO_3$, $CaCO_3$ and $BaCO_3$; boron oxide ($B_2O_3$).

The catalytically active composition of the catalysts of the invention and the catalysts used in the process of the invention preferably does not comprise any ruthenium, any iron and/or any zinc.

The catalytically active composition of the catalyst prior to reduction with hydrogen preferably comprises from 0.1 to 10% by weight, particularly preferably from 0.2 to 7% by weight, more preferably from 0.4 to 5% by weight, of oxygen-comprising compounds of one or more metals selected from among Pb, Bi, Sn, Sb and in, in each case calculated as PbO, $Bi_2O_3$, SnO, $Sb_2O_3$ or $In_2O_3$.

The metal is particularly preferably selected from among Pb, Bi and In.

The catalytically active composition of the catalyst prior to reduction with hydrogen also preferably comprises
from 10 to 75% by weight, particularly preferably from 25 to 65% by weigh, more preferably from 30 to 55% by weight, of oxygen-comprising compounds of zirconium, calculated as $ZrO_2$,
from 1 to 30% by weight, particularly preferably from 2 to 25% by weight, more preferably from 5 to 15% by weight, of oxygen-comprising compounds of copper, calculated as CuO,
from 10 to 50% by weight, particularly preferably from 13 to 40% by weight, more preferably from 16 to 35% by weight, of oxygen-comprising compounds of nickel, calculated as NiO, and
from 10 to 50% by weight, particularly preferably from 13 to 40% by weight, more preferably from 16 to 35% by weight, of oxygen-comprising compounds of cobalt, calculated as CoO.

The molar ratio of nickel to copper is preferably greater than 1, particularly preferably greater than 1.2, more particularly preferably in the range from 1.8 to 8.5.

The catalysts used in the process of the invention can be produced by various methods. They can be obtained, for example, by peptizing pulverulent mixtures of hydroxides, carbonates, oxides and/or other salts of the components with water and subsequently extruding and heat treating the mass obtained in this way.

Precipitation methods are preferably employed for producing the catalysts of the invention. Thus, they can be obtained, for example, by coprecipitation of the nickel, cobalt and copper and dopant metal components from an aqueous salt solution comprising these elements by means of bases in the presence of a slurry of a sparingly soluble, oxygen-comprising zirconium compound and subsequent washing, drying and calcination of the precipitate obtained. As sparingly soluble, oxygen-comprising zirconium compounds, it is possible to use, for example, zirconium dioxide, zirconium oxide hydrate, zirconium phosphates, borates and silicates. The slurries of the sparingly soluble zirconium compounds can be produced by suspending finely divided powder of these compounds in water with vigorous stirring. These slurries are advantageously obtained by precipitation of sparingly soluble zirconium compounds from aqueous zirconium salt solutions by means of bases.

The catalysts of the invention are preferably produced by coprecipitation. For this purpose, an aqueous salt solution comprising the catalyst components is advantageously admixed hot and while stirring with an aqueous base, for example sodium carbonate, sodium hydroxide, potassium carbonate or potassium hydroxide, until precipitation is complete. However, bases which are free of alkali metal, e.g. ammonia, ammonium carbonate, ammonium hydrogencarbonate, ammonium carbamate, ammonium oxalate, ammonium malonate, urotropin, urea, etc., can also be employed. The type of salts used is generally not critical: since the main important factor in this procedure is the water-solubility of the salts, a criterion is that they have the good solubility in water required for producing these relatively highly concentrated salt solutions. It is considered self-evident that, when choosing the salts of the individual components, the salts chosen are naturally only ones which have anions which do not lead to problems, whether by causing undesirable precipitation or by hindering or preventing precipitation as a result of complex formation.

The precipitates obtained in these precipitation reactions are generally chemically nonuniform and comprise, inter alia, mixtures of the oxides, oxide hydrates, hydroxides, carbonates and insoluble and basic salts of the metals used. To improve the filterability of the precipitates, it can be found to be useful for them to be aged, i.e. for them to be left to stand for some time after precipitation, if appropriate at elevated temperature or with air being passed through the suspension.

The precipitates obtained by these precipitation processes are processed further in a customary fashion to give the catalysts of the invention. The precipitates are firstly washed. The content of the alkali metal which has been introduced via any (mineral) base used as precipitant can be influenced via the duration of the washing procedure and via the temperature and amount of the washing water. In general, an increase in the washing time or an increase in the temperature of the washing water results in a decrease in the alkali metal content. After washing, the precipitated material is generally dried at from 80 to 200° C., preferably from 100 to 150° C., and then calcined. Calcination is generally carried out at temperatures of from 300 to 800° C., preferably from 400 to 600° C., in particular from 450 to 550° C.

The catalysts of the invention can also be produced by impregnation of zirconium dioxide ($ZrO_2$) which is, for example, present in the form of powder or shaped bodies such as extrudates, pellets, spheres or rings.

The zirconium dioxide is used, for example, in the monoclinic or tetragonal form, preferably in the monoclinic form.

The shaped bodies can be produced by the customary methods.

The impregnation is likewise carried out by customary methods, as described, for example, in A. B. Stiles, Catalyst Manufacture—Laboratory and Commercial Preparations, Marcel Dekker, New York (1983), by application of an appropriate metal salt solution in one or more impregnation stages using, for example, appropriate nitrates, acetates or chlorides as metal salts. After impregnation, the composition is dried and optionally calcined.

Impregnation can also be carried out by the "incipient wetness" method in which the zirconium dioxide is moistened at most to saturation with the impregnation solution, in accordance with its water absorption capacity. However, impregnation can also be carried out in an excess of solution.

In the case of multistage impregnation processes, it is advantageous to dry and optionally calcine the material being impregnated between individual impregnation steps. Multistage impregnation is particularly advantageous when the zirconium dioxide is to be loaded with a relatively large amount of metal.

To apply the metal components to the zirconium dioxide, the impregnation can be carried out using all metal salts simultaneously or using these individual metal salts successively in any order.

The catalysts produced by impregnation are subsequently dried and preferably also calcined, e.g. in the calcination temperature ranges indicated above.

After calcination, the catalyst is advantageously conditioned either by milling it to a particular particle size or by mixing it after milling with shaping aids such as graphite or stearic acid, pressed by means of a press to form shaped bodies, e.g. pellets, and heat treated. The heat treatment temperatures preferably correspond to the temperatures in the calcination.

The catalysts produced in this way comprise the catalytically active metals in the form of a mixture of their oxygen-comprising compounds, i.e. in particular as oxides and mixed oxides.

The catalysts produced, for example, as described above are stored as such and, if appropriate, sold. Before use as catalysts, they are usually prereduced. However, they can also be used without prereduction, in which case they are then reduced by the hydrogen present in the reactor under the conditions of the hydrogenative amination.

To carry out the prereduction, the catalysts are firstly exposed to a nitrogen/hydrogen atmosphere at preferably from 150 to 200° C. for a period of, for example, from 12 to 20 hours and subsequently treated in a hydrogen atmosphere at preferably from 200 to 400° C. for up to about 24 hours. In this prereduction, part of the oxygen-comprising metal compounds present in the catalysts is reduced to the corresponding metals, so that the latter are present together with the various oxygen compounds in the active form of the catalyst.

A further advantage of the catalysts of the invention is their mechanical stability, i.e. their hardness. The mechanical stability can be determined by measuring the lateral compressive strength. For this purpose, the shaped catalyst body, e.g. the catalyst pellet, is loaded under increasing force between two parallel plates, with this loading being able to occur, for example, on the cylindrical surface of catalyst pellets, until fracture of the shaped catalyst body occurs. The force recorded on fracture of the shaped catalyst body is the lateral compressive strength.

The process of the invention is preferably carried out continuously, with the catalyst preferably being arranged as a fixed bed in the reactor. Flow into the fixed catalyst bed can occur either from above or from below. The temperature, pressure and amount of the gas stream are set so that even relatively high-boiling reaction products remain in the gas phase.

The aminating agent can be used in stoichiometric, substoichiometric or superstoichiometric amounts based on the alcoholic hydroxyl group or aldehyde group or keto group to be aminated.

In the case of amination of alcohols, aldehydes or ketones by means of primary or secondary amines, the amine is preferably used in an approximately stoichiometric amount or slightly superstoichiometric amount per mole of alcoholic hydroxyl group, aldehyde group or keto group to be aminated.

The amine component (nitrogen compound) is preferably used in a from 0.90- to 100-fold molar amount, in particular in a from 1.0- to 10-fold molar amount, based in each case on the alcohol, aldehyde and/or ketone used.

Ammonia specifically is generally used in a from 1.5- to 250-fold, preferably from 2- to 100-fold, in particular from 2- to 10-fold, molar excess per mole of alcoholic hydroxyl group, aldehyde group or keto group to be reacted. Larger excesses both of ammonia and of primary or secondary amines are possible.

The process is preferably operated with an amount of off-gas of from 5 to 800 standard cubic meters/h, in particular from 20 to 300 standard cubic meters/h.

The amination of the primary or secondary alcohol groups, aldehyde groups or keto groups of the starting material can be carried out in the liquid phase or in the gas phase. Preference is given to a fixed-bed process in the gas phase.

When the process is carried out in the liquid phase, the starting materials (alcohol, aldehyde or ketone plus ammonia or amine) are passed simultaneously in the liquid phase at pressures of generally from 5 to 30 MPa (50-300 bar), preferably from 5 to 25 MPa, particularly preferably from 15 to 25 MPa, and temperatures of generally from 80 to 350° C., in particular from 100 to 300° C., preferably from 120 to 270° C., particularly preferably from 130 to 250° C., especially from 170 to 230° C., including hydrogen over the catalyst which is usually located in a fixed-bed reactor which is preferably heated from the outside. The reactor can be operated either in the downflow mode or in the upflow mode. The space velocity over the catalyst is generally in the range from 0.05 to 5 kg, preferably from 0.1 to 2 kg, particularly preferably from 0.2 to 0.6 kg, of alcohol, aldehyde or ketone per liter of catalyst (bed volume) and hour. If appropriate, the starting materials can be diluted with a suitable solvent such as tetrahydrofuran, dioxane, N-methylpyrrolidone or ethylene glycol dimethyl ether. It is advantageous to heat the reactants before they are introduced into the reaction vessel, preferably to the reaction temperature.

When the process is carried out in the gas phase, the gaseous starting materials (alcohol, aldehyde or ketone plus ammonia or amine) are passed in a gas stream which is sufficiently large for vaporization, preferably hydrogen, at pressures of generally from 0.1 to 40 MPa (from 1 to 400 bar), preferably from 0.1 to 10 MPa, particularly preferably from 0.1 to 5 MPa, in the presence of hydrogen over the catalyst. The temperatures for the amination of alcohols are generally from 80 to 350° C., in particular from 100 to 300° C., preferably from 120 to 270° C., particularly preferably from 160 to 250° C. The reaction temperatures in the hydrogenative amination of aldehydes and ketones are generally from 80 to 350° C., in particular from 90 to 300° C., preferably from 100 to 250° C. Flow into the fixed catalyst bed can occur either from above or from below. The gas stream required is preferably obtained by means of a gas recycle mode of operation.

The space velocity of the catalyst is generally in the range from 0.01 to 2 kg, preferably from 0.05 to 0.5 kg, of alcohol, aldehyde or ketone per liter of catalyst (bed volume) and hour.

The hydrogen is generally fed to the reaction in an amount of from 5 to 400 l, preferably in an amount of from 50 to 200 l, per mole of alcohol, aldehyde or ketone component, with the amounts in liters in each case being at S.T.P.

The amination of aldehydes or ketones differs from the procedure in the amination of alcohols in that at least stoichiometric amounts of hydrogen have to be present in the amination of aldehydes and ketones.

Both when the process is carried out in the liquid phase and when it is carried out in the gas phase, it is possible to employ higher temperatures and higher total pressures and space velocities over the catalyst. The pressure in the reaction vessel, which is the sum of the partial pressures of the aminating agent, the alcohol, aldehyde or ketone and the reaction products formed and also any solvent used at the temperatures indicated, is advantageously increased to the desired reaction pressure by injection of hydrogen.

Both when the process is carried out continuously in the liquid phase and when it is carried out continuously in the gas phase, the excess aminating agent can be circulated together with the hydrogen.

If the catalyst is arranged as a fixed bed, it can be advantageous in terms of the selectivity of the reaction for the shaped catalyst bodies in the reactor to be mixed with inert packing elements, i.e. to "dilute" them. The proportion of packing elements in such catalyst preparations can be from 20 to 80 parts by volume, particularly preferably from 30 to 60 parts by volume and in particular from 40 to 50 parts by volume.

The water of reaction formed during the course of the reaction (in each case one mole per mole of alcohol group, aldehyde group or keto group reacted) generally does not have any adverse effect on the conversion, the reaction rate, the selectivity and the operating life of the catalyst and is therefore advantageously removed from the reaction product only during the work-up of the latter, e.g. by distillation.

After the output from the reactor has advantageously been depressurized, the excess hydrogen and any excess aminating agent present are removed and the crude reaction product is purified, e.g. by fractional rectification. Suitable work-up methods are described, for example, in EP-A-1 312 600 and EP-A-1 312 599 (both BASF AG). The excess aminating agent and the hydrogen are advantageously recirculated to the reaction zone. The same applies to any incompletely reacted alcohol, aldehyde or ketone component.

Unreacted starting materials and any suitable by-products formed can be recirculated to the synthesis. Unreacted starting materials can, after condensation of the products in a separator, be passed batchwise or continuously over the catalyst bed again in the circulating gas stream.

Aminating agents in the process of the invention are ammonia and primary and secondary amines.

The process of the invention can be used to prepare, for example, amines of the formula I

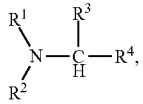

where
- $R^1$, $R^2$ are each hydrogen (H), alkyl such as $C_{1-20}$-alkyl, cycloalkyl such as $C_{3-12}$-cycloalkyl, alkoxyalkyl such as $C_{2-30}$-alkoxyalkyl, dialkylaminoalkyl such as $O_{3-30}$-dialkylaminoalkyl, aryl, aralkyl such as $C_{7-20}$-aralkyl and alkylaryl such as $C_{7-20}$-alkylaryl, or together form —$(CH_2)_j$—X—$(CH_2)_k$—,
- $R^3$, $R^4$ are each hydrogen (H), alkyl such as $C_{1-20}$-alkyl, cycloalkyl such as $C_{3-12}$-cycloalkyl, hydroxyalkyl such as $C_{1-20}$-hydroxyalkyl, aminoalkyl such as $C_{1-20}$-aminoalkyl, hydroxyalkylaminoalkyl such as $C_{2-20}$-hydroxyalkylaminoalkyl, alkoxyalkyl such as $C_{2-30}$-, dialkylaminoalkyl such as $C_{3-30}$-dialkylaminoalkyl, alkylaminoalkyl such as $C_{2-30}$-alkylaminoalkyl, $R^5$—$(OCR^6R^7CR^8R^9)_n$—$(OCR^6R^7)$, aryl, heteroaryl, aralkyl such as $C_{7-20}$-aralkyl, heteroarylalkyl such as $C_{4-20}$-heteroarylalkyl, alkylaryl such as $C_{7-20}$-alkylaryl, alkylheteroaryl such as $C_{4-20}$-alkylheteroaryl and Y—$(CH_2)_m$—$NR^5$—$(CH_2)_q$ or together form —$(CH_2)_l$—X—$(CH_2)_m$— or
- $R^2$ and $R^4$ together form —$(CH_2)_l$—X—$(CH_2)_m$—,
- $R^5$, $R^{10}$ are each hydrogen (H), alkyl such as $C_{1-4}$-alkyl, alkylphenyl such as $C_{7-40}$-alkylphenyl,
- $R^6$, $R^7$, $R^8$, $R^9$ are each hydrogen (H), methyl or ethyl,
- X is $CH_2$, $CHR^5$, oxygen (O), sulfur (S) or $NR^5$,
- Y is $N(R^{10})_2$, hydroxy, $C_{2-20}$-alkylaminoalkyl or $C_{3-20}$-dialkylaminoalkyl,
- n is an integer from 1 to 30 and
- j, k, l, m, q are each an integer from 1 to 4.

The process of the invention is therefore preferably employed for preparing an amine I by reacting a primary or secondary alcohol of the formula II

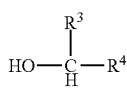

and/or aldehyde and/or ketone of the formula VI or VII

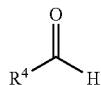

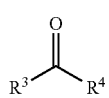

with a nitrogen compound of the formula III

where $R^1$, $R^2$, $R^3$ and $R^4$ are as defined above.

The starting alcohol can also be an amino alcohol, e.g. an amino alcohol of the formula II.

As the definitions of the radicals $R^2$ and $R^4$ indicate, the reaction can also occur intramolecularly in an appropriate amino alcohol, amino ketone or amino aldehyde.

Accordingly, to prepare the amine I, a hydrogen atom of the nitrogen compound III is replaced purely formally by the radical $R^4(R^3)CH$— with liberation of one molar equivalent of water.

Preference is also given to employing the process of the invention in the Preparation of a cyclic amine of the formula IV

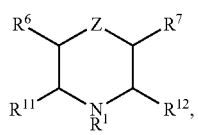

where
- $R^{11}$ and $R^{12}$ are each hydrogen (H), alkyl such as $C_1$-$C_{20}$-alkyl, cycloalkyl such as $C_3$-$C_{12}$-cycloalkyl, aryl, heteroaryl, aralkyl such as $C_7$-$C_{20}$-aralkyl and alkylaryl such as $C_7$-$C_{20}$-alkylaryl,
- Z is $CH_2$, $CHR^5$, oxygen (O), $NR^5$ or $NCH_2CH_2OH$ and
- $R^1$, $R^6$, $R^7$ are as defined above, by reaction of an alcohol of the formula V

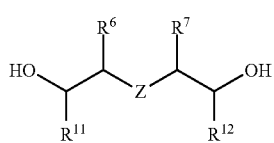

with ammonia or a primary amine of the formula VI

$R^1$—$NH_2$ (VI).

The substituents $R^1$ to $R^{12}$, the variables X, Y, Z and the indices j, k, l, m, n and q in the compounds I, II, III, IV, V, VI and VII have, independently of one another, the following meanings:

$R^1, R^2, R^3, R^4, R^5, R^6, R^7, R^8, R^9, R^{10}, R^{11}, R^{12}$:
  hydrogen (H), $R^3, R^4$:
  alkyl such as $C_{1-20}$-alkyl, preferably $C_{1-14}$-alkyl such as methyl, ethyl, n-propyl, isopropyl, n-butyl, isobutyl, sec-butyl, tert-butyl, n-pentyl, isopentyl, sec-pentyl, neo-pentyl, 1,2-dimethylpropyl, n-hexyl, isohexyl, sec-hexyl, cyclopentylmethyl, n-heptyl, isoheptyl, cyclohexylmethyl, n-octyl, isooctyl, 2-ethylhexyl, n-decyl, 2-n-propyl-n-heptyl, n-tridecyl, 2-n-butyl-n-nonyl and 3-n-butyl-n-nonyl,
  hydroxyalkyl such as $C_{1-20}$-hydroxyalkyl, preferably $C_{1-8}$-hydroxyalkyl, particularly preferably $C_{1-4}$-hydroxyalkyl such as hydroxymethyl, 1-hydroxyethyl, 2-hydroxyethyl, 1-hydroxy-n-propyl, 2-hydroxy-n-propyl, 3-hydroxy-n-propyl and 1-(hydroxymethyl)ethyl,
  aminoalkyl such as $C_{1-20}$-aminoalkyl, preferably $C_{1-8}$-aminoalkyl such as aminomethyl, 2-aminoethyl, 2-amino-1,1-dimethylethyl, 2-amino-n-propyl, 3-amino-n-propyl, 4-amino-n-butyl, 5-amino-n-pentyl, N-(2-aminoethyl)-2-aminoethyl and N-(2-aminoethyl)aminomethyl,
  hydroxyalkylaminoalkyl such as $C_{2-20}$-hydroxyalkylaminoalkyl, preferably $C_{3-8}$-hydroxyalkylaminoalkyl such as (2-hydroxyethylamino)methyl, 2-(2-hydroxyethylamino)ethyl and 3-(2-hydroxyethylamino)propyl,
  $R^5$—$(OCR^6R^7CR^8R^9)_n$—$(OCR^6R^7)$, preferably $R^5$—$(OCHR^7CHR^9)_n$—$(OCR^6R^7)$, particularly preferably $R^5$—$(OCH_2CHR^9)_n$—$(OCR^6R^7)$,
  alkylaminoalkyl such as $C_{2-30}$-alkylaminoalkyl, preferably $C_{2-20}$-alkylaminoalkyl, particularly preferably $C_{2-8}$-alkylaminoalkyl such as methylaminomethyl, 2-methylaminoethyl, ethylaminomethyl, 2-ethylaminoethyl and 2-(isopropylamino)ethyl, $(R^5)HN$—$(CH_2)_q$, $Y$—$(CH_2)_m$—$NR^5$—$(CH_2)_q$,
  heteroarylalkyl such as $C_{4-20}$-heteroarylalkyl, e.g. pyrid-2-ylmethyl, furan-2-yl-methyl, pyrrol-3-ylmethyl and imidazol-2-ylmethyl,
  alkylheteroaryl such as $C_{4-20}$-alkylheteroaryl, e.g. 2-methyl-3-pyridinyl, 4,5-dimethylimidazol-2-yl, 3-methyl-2-(uranyl and 5-methyl-2-pyrazinyl,
  heteroaryl such as 2-pyridinyl, 3-pyridinyl, 4-pyridinyl, pyrazinyl, pyrrol-3-yl, imidazol-2-yl, 2-furanyl and 3-furanyl, $R^1, R^2, R^3, R^4$:
  cycloalkyl such as $C_{3-12}$-cycloalkyl, preferably $C_{3-8}$-cycloalkyl such as cyclopropyl, cyclobutyl, cyclopentyl, cyclohexyl, cycloheptyl and cyclooctyl, particularly preferably cyclopentyl and cyclohexyl,
  alkoxyalkyl such as $C_{2-30}$-alkoxyalkyl, preferably $C_{2-20}$-alkoxyalkyl, particularly preferably $C_{2-8}$-alkoxyalkyl such as methoxymethyl, ethoxymethyl, n-propoxymethyl, isopropoxymethyl, n-butoxymethyl, isobutoxymethyl, sec-butoxymethyl, tert-butoxymethyl, 1-methoxyethyl and 2-methoxyethyl, particularly preferably $C_{2-4}$-alkoxyalkyl,
  dialkylaminoalkyl such as $C_{3-30}$-dialkylaminoalkyl, preferably $C_{3-20}$-dialkylaminoalkyl, particularly preferably $C_{3-10}$-dialkylaminoalkyl such as N,N-dimethylaminomethyl, (N,N-dibutylamino)methyl, 2-(N,N-dimethylamino)ethyl, 2-(N,N-diethylamino)ethyl, 2-(N,N-dibutylamino)ethyl, 2-(N,N-di-n-propylamino)ethyl and 2-(N,N-diisopropylamino)ethyl, 3-(N,N-dimethylamino)propyl, $(R^5)_2N$—$(CH_2)_q$,
  aryl such as phenyl, 1-naphthyl, 2-naphthyl, 1-anthryl, 2-anthryl and 9-anthryl, preferably phenyl, 1-naphthyl and 2-naphthyl, particularly preferably phenyl,
  alkylaryl such as $C_{7-20}$-alkylaryl, preferably $C_{7-12}$-alkylphenyl such as 2-methylphenyl, 3-methylphenyl, 4-methylphenyl, 2,4-dimethylphenyl, 2,5-dimethylphenyl, 2,6-dimethylphenyl, 3,4-dimethylphenyl, 3,5-dimethylphenyl, 2,3,4-trimethylphenyl, 2,3,5-trimethylphenyl, 2,3,6-trimethylphenyl, 2,4,6-trimethylphenyl, 2-ethylphenyl, 3-ethylphenyl, 4-ethylphenyl, 2-n-propylphenyl, 3-n-propylphenyl and 4-n-propylphenyl,
  aralkyl such as $C_{7-20}$-aralkyl, preferably $C_{7-12}$-phenylalkyl such as benzyl, p-methoxybenzyl, 3,4-dimethoxybenzyl, 1-phenethyl, 2-phenethyl, 1-phenylpropyl, 2-phenylpropyl, 3-phenylpropyl, 1-phenylbutyl, 2-phenylbutyl, 3-phenylbutyl and 4-phenylbutyl, particularly preferably benzyl, 1-phenethyl and 2-phenethyl, $R^3$ and $R^4$ or $R^2$ and $R^4$ together a —$(CH_2)_l$—X—$(CH_2)_m$— group such as —$(CH_2)_3$—, —$(CH_2)_4$—, —$(CH_2)_5$—, —$(CH_2)_6$—, —$(CH_2)_7$—, —$(CH_2)$—O—$(CH_2)_2$—, —$(CH_2)$—$NR^5$—$(CH_2)_2$—, —$(CH_2)$—$CHR^5$—$(CH_2)_2$—, —$(CH_2)_2$—O—$(CH_2)_2$—, —$(CH_2)_2$—$NR^5$—$(CH_2)_2$—, —$(CH_2)_2$—$CHR^5$—$(CH_2)_2$—, —$CH_2$—O—$(CH_2)_3$—, —$CH_2$—$NR^5$—$(CH_2)_3$—, —$CH_2$—$CHR^5$—$(CH_2)_3$—, $R^1, R^2$:
  alkyl such as $C_{1-20}$-alkyl, preferably $C_{1-5}$-alkyl such as methyl, ethyl, n-propyl, isopropyl, n-butyl, isobutyl, sec-butyl, tert-butyl, n-pentyl, isopentyl, sec-pentyl, neo-pentyl, 1,2-dimethylpropyl, n-hexyl, isohexyl, sec-hexyl, n-heptyl, isoheptyl, n-octyl, isooctyl, 2-ethylhexyl, particularly preferably $C_{1-4}$-alkyl, or $R^1$ and $R^2$ together a —$(CH_2)_j$—X—$(CH_2)_k$— group such as —$(CH_2)_3$—, —$(CH_2)_4$—, —$(CH_2)_5$—, —$(CH_2)_6$—, —$(CH_2)_7$—, —$(CH_2)$—O—$(CH_2)_2$—, —$(CH_2)$—$NR^5$—$(CH_2)_2$—, —$(CH_2)$—$CHR^5$—$(CH_2)_2$—, —$(CH_2)_2$—O—$(CH_2)_2$—, —$(CH_2)_2$—$NR^5$—$(CH_2)_2$—, —$(CH_2)_2$—$CHR^5$—$(CH_2)_2$, —$CH_2$—O—$(CH_2)_3$—, —$CH_2$—$NR^5$—$(CH_2)_3$—, —$CH_2$—$CHR^5$—$(CH_2)_3$—, $R^5, R^{10}$:
  alkyl, preferably $C_{1-4}$-alkyl such as methyl, ethyl, n-propyl, isopropyl, n-butyl, isobutyl, sec-butyl and tert-butyl, preferably methyl and ethyl, particularly preferably methyl,
  alkylphenyl, preferably $C_{7-40}$-alkylphenyl such as 2-methylphenyl, 3-methylphenyl, 4-methylphenyl, 2,4-dimethylphenyl, 2,5-dimethylphenyl, 2,6-dimethylphenyl, 3,4-dimethylphenyl, 3,5-dimethylphenyl, 2-, 3-, 4-nonylphenyl, 2-, 3-, 4-decylphenyl, 2,3-, 2,4-, 2,5-, 3,4-, 3,5-dinonylphenyl, 2,3-, 2,4-, 2,5-, 3,4- and 3,5-didecylphenyl, in particular $C_{7-20}$-alkylphenyl, $R^6, R^7, R^8, R^9$:
  methyl or ethyl, preferably methyl, $R^{11}, R^{12}$:
  alkyl such as $C_1$-$C_{20}$-alkyl, cycloalkyl such as $C_3$-$C_{12}$-cycloalkyl, aryl, heteroaryl, aralkyl such as $C_7$-$C_{20}$-aralkyl and alkylaryl such as $C_7$-$C_{20}$-alkylaryl, in each case as defined above, X:
  $CH_2$, $CHR^5$, oxygen (O), sulfur (S) or $NR^5$, preferably $CH_2$ and O, Y:
  $N(R^{10})_2$, preferably $NH_2$ and $N(CH_3)_2$,
  hydroxy (OH),
  $C_{2-20}$-alkylaminoalkyl, preferably $C_{2-16}$-alkylaminoalkyl such as methylaminomethyl, 2-methylaminoethyl, ethylaminomethyl, 2-ethylaminoethyl and 2-(isopropylamino)ethyl, C$_{3-20}$-dialkylaminoalkyl, preferably C$_{3-16}$-dialkylaminoalkyl such as dimethylaminomethyl, 2-dimethylaminoethyl, 2-diethylaminoethyl, 2-(di-n-propylamino)ethyl and 2-(diisopropylamino)ethyl, Z:
CH$_2$, CHR$^5$, O, NR$^5$ or NCH$_2$CH$_2$OH, j, l:
an integer from 1 to 4 (1, 2, 3 or 4), preferably 2 and 3, particularly preferably 2, k, m, q:
an integer from 1 to 4 (1, 2, 3 or 4), preferably 2, 3 and 4, particularly preferably 2 and 3, n:
an integer from 1 to 30, preferably an integer from 1 to 8 (1, 2, 3, 4, 5, 6, 7 or 8), particularly preferably an integer from 1 to 6.

Suitable alcohols are, subject to the abovementioned conditions, virtually all primary and secondary alcohols having an aliphatic OH function. The alcohols can be linear, branched or cyclic. Secondary alcohols are aminated just like primary alcohols. The alcohols can also bear substituents or comprise functional groups which are inert under the conditions of the hydrogenative amination, for example alkoxy, alkenyloxy; alkylamino or dialkylamino groups, or may be hydrogenated under the conditions of the hydrogenative amination, for example CC double or triple bonds. If polyhydric alcohols are to be aminated, it is possible to obtain amino alcohols, cyclic amines or multiply aminated products preferentially by controlling the reaction conditions.

The amination of 1,4-diols leads, depending on the choice of reaction conditions, to 1-amino-4-hydroxy compounds, 1,4-diamino compounds or five-membered rings containing a nitrogen atom (pyrrolidines).

The amination of 1,6-diols leads, depending on the choice of reaction conditions, to 1-amino-6-hydroxy compounds, 1,6-diamino compounds or seven-membered rings containing a nitrogen atom (hexamethylenimines).

The amination of 1,5-diols leads, depending on the choice of reaction conditions, to 1-amino-5-hydroxy compounds, 1,5-diamino compounds or six-membered rings containing a nitrogen atom (piperidines, 1,5-dipiperidinylpentane). Accordingly, amination of diglycol (DEG) by means of NH$_3$ can give monoaminodiglycol (=ADG=H$_2$N—CH$_2$CH$_2$—O—CH$_2$CH$_2$—OH), diaminodiglycol CH$_2$N—CH$_2$CH$_2$—O—CH$_2$CH$_2$—NH$_2$) or particularly preferably morpholine. Correspondingly, piperazine is particularly preferably obtained from diethanolamine. N-(2-hydroxyethyl)piperazine can be obtained from triethanolamine.

Preference is given to aminating, for example, the following alcohols:
methanol, ethanol, n-propanol, isopropanol, n-butanol, isobutanol, n-pentanol, n-hexanol, 2-ethylhexanol, tridecanol, stearyl alcohol, palmityl alcohol, cyclobutanol, cyclopentanol, cyclohexanol, benzyl alcohol, 2-phenylethanol, 2-(p-methoxyphenyl)-ethanol, 2-(3,4-dimethoxyphenyl)ethanol, 1-phenyl-3-butanol, ethanolamine, n-propanolamine, isopropanolamine, 2-amino-1-propanol, 1-methoxy-2-propanol, 3-amino-2,2-dimethyl-1-propanol, n-pentanolamine (1-amino-5-pentanol), n-hexanolamine (1-amino-6-hexanol), ethanolamine, diethanolamine, triethanolamine, N-alkyldiethanol-amines, diisopropanolamine, 3-(2-hydroxyethylamino)propan-1-ol, 2-(N,N-dimethylamino)ethanol, 2-(N,N-diethylamino)ethanol, 2-(N,N-di-n-propylamino)ethanol, 2-(N,N-diisopropylamino)ethanol, 2-(N,N-di-n-butylamino)ethanol, 2-(N,N-diisobutyl-amino)ethanol, 2-(INN-di-sec-butylamino)ethanol, 2-(N,N-di-tert-butylamino)ethanol, 3-(N,N-dimethylamino)propanol, 3-(N,N-diethylamino)propanol, 3-(N,N-di-n-propylamino)propanol, 3-(N,N-diisopropylamino)propanol, 3-(N,N-di-n-butylamino)propanol, 3-(N,N-diisobutylamino)propanol, 3-(N,N-di-sec-butylamino)propanol, 3-(N,N-di-tert-butylamino)propanol, 1-dimethylamino-4-pentanol, 1-diethylamino-4-pentanol, ethylene glycol, 1,2-propylene glycol, 1,3-propylene glycol, diglycol, 1,4-butanediol, 1,5-pentanediol, 1,6-hexanediol, 2,2-bis[4-hydroxycyclohexyl]propane, methoxyethanol, propoxyethanol, butoxyethanol, polypropyl alcohols, polyethylene glycol ethers, polypropylene glycol ethers and polybutylene glycol ethers. In the process of the invention, the polyalkylene glycol ethers mentioned last are converted into the corresponding amines by transformation of their free hydroxyl groups.

Particularly preferred alcohols are methanol, ethanol, n-propanol, isopropanol, n-butanol, sec-butanol, 1,4-butanediol, 1,5-pentanediol, 1,6-hexanediol, 2-ethylhexanol, cyclohexanol, fatty alcohols, ethylene glycol, diethylene glycol (DEG), triethylene glycol (TEG), 2-(2-di methylaminoethoxy)ethanol, N-methyldiethanolamine and 2-(2-di-methylaminoethoxy)ethanol.

Ketones which can be used in the process of the invention subject to the abovementioned conditions are virtually all aliphatic and aromatic ketones. The aliphatic ketones can be linear, branched or cyclic, and the ketones can comprise heteroatoms. The ketones can also bear substituents or comprise functional groups which are inert under the conditions of the hydrogenative amination, for example alkoxy, alkenyloxy, alkylamino or dialkylamino groups, or may also be hydrogenated under the conditions of the hydrogenative amination, for example CC double or triple bonds. If polyfunctional ketones are to be aminated, amino ketones, amino alcohols, cyclic amines or multiply aminated products can be obtained by controlling the reaction conditions.

Preference is given to aminatively hydrogenating, for example, the following ketones:
acetone, ethyl methyl ketone, methyl vinyl ketone, isobutyl methyl ketone, butanone, 3-methylbutan-2-one, diethyl ketone, tetralone, acetophenone, p-methylacetophenone, p-methoxyacetophenone, m-methoxyacetophenone, 1-acetylnaphthalene, 2-acetyl-naphthalene, 1-phenyl-3-butanone, cyclobutanone, cyclopentanone, cyclopentenone, cyclohexanone, cyclohexenone, 2,6-dimethylcyclohexanone, cycloheptanone, cyclododecanone, acetylacetone, methylglyoxal and benzophenone. Aldehydes which can be used in the process of the invention subject to the abovementioned conditions are virtually all aliphatic and aromatic aldehydes. The aliphatic aldehydes can be linear, branched or cyclic, and the aldehydes can comprise heteroatoms. The aldehydes can also bear substituents or comprise functional groups Which are inert under the conditions of the hydrogenative amination, for example alkoxy, alkenyloxy, alkylamino or dialkylamino groups, or may also be hydrogenated under the conditions of the hydrogenative amination, for example CC double or triple bonds. If polyfunctional aldehydes or keto aldehydes are to be aminated, amino alcohols, cyclic amines or multiply aminated products can be obtained by controlling the reaction conditions.

Preference is given to aminatively hydrogenating, for example, the following aldehydes:
formaldehyde, acetaldehyde, propionaldehyde, n-butyraldehyde, isobutyraldehyde, pivalaldehyde, n-pentanal, n-hexanal, 2-ethylhexanal, 2-methylpentanal, 3-methylpentanal, 4-methylpentanal, glyoxal, benzaldehyde, p-methoxybenzaldehyde, p-methylbenzaldehyde, phenylacetaldehyde, (p-methoxyphenyl)acetaldehyde, (3,4-dimethoxyphenyl)acetaldehyde, 4-formyltetrahydropyran, 3-formyltetrahydrofuran, 5-formylvaleronitrile, citronellal, lysmeral, acrolein, methacrolein, ethylacrolein, citral, crotonaldehyde, 3-methoxypropionaldehyde, 3-aminopropionaldehyde, hydroxypivalalaldehyde, dimethylolpropionaldehyde, dimethylolbutyraldehyde, furfural, glyoxal, glutaraldehyde and also hydroformylated oligomers and polymers, e.g. hydroformylated polyisobutene (polyisobutene aldehyde) or the oligomer obtained by metathesis of 1-pentene and cyclopentene and hydroformylated.

As aminating agent in the hydrogenative amination of alcohols, aldehydes or ketones in the presence of hydrogen, it is possible to use either ammonia or primary or secondary, aliphatic or cycloaliphatic or aromatic amines.

When ammonia is used as aminating agent, the alcoholic hydroxyl group or the aldehyde group or the keto group is firstly converted into a primary amino group ($—NH_2$) The primary amine formed in this way can react with further alcohol or aldehyde or ketone to form the corresponding secondary amine and this can in turn react with further alcohol or aldehyde or ketone to form the corresponding, preferably symmetrical, tertiary amine. Depending on the composition of the reaction mixture or the feed stream (in the case of continuous operation) and depending on the reaction conditions employed, viz. pressure, temperature, reaction time (space velocity over the catalyst), primary, secondary or tertiary amines can be prepared preferentially as desired in this way.

Polyhydric alcohols or dialdehydes or oligoaldehydes or diketones or oligoketones or keto aldehydes can in this way be converted by intramolecular hydrogenative amination into cyclic amines such as pyrrolidines, piperidines, hexamethylenimines, piperazines and morpholines.

Primary or secondary amines can also be used like ammonia as aminating agents.

These aminating agents are preferably used for preparing unsymmetrically substituted dialkylamines or trialkylamines, e.g. ethyldiisopropylamine and ethyldicyclohexylamine. For example, the following mohoalkylamines and dialkylamines are used as aminating agents: monomethylamine, dimethylamine, monoethylamine, diethylamine, n-propylamine, di-n-propylamine, isopropylamine, diisopropylamine, isopropylethylamine, n-butylamine, di-n-butylamine, s-butylamine, di-s-butylamine, isobutylamine, n-pentylamine, s-pentylamine, isopentylamine, n-hexylamine, s-hexylamine, isohexylamine, cyclohexylamine, aniline, toluidine, piperidine, morpholine and pyrrolidine.

Amines which are particularly preferably prepared by the process of the invention are, for example, morpholine (from monoaminodiglycol), monoaminodiglycol, morpholine and/or bis(2-morpholinoethyl)ether (DMDEE) (from DEG and ammonia), 6-dimethylamino-1-hexanol (from hexanediol and dimethylamine (DMA)), triethylamine (from ethanol and diethylamine (DEA)), dimethylethylamine (from ethanol and DMA), N—($C_{1-4}$-alkyl)morpholine (from DEG and mono ($C_{1-4}$-alkyl)amine), N—($C_{1-4}$-alkyl)piperidine (from 1,5-pentanedial and mono($C_{1-4}$-alkyl)amine), piperazine and/or diethylenetriamine (DETA) (from N-(2-aminoethyl)ethanolamine (AEEA) and ammonia), N-methyl-piperazine (from diethanolamine and MMA), N,N'-dimethylpiperazine (from N-methyl-diethanolamine and MMA), 1,2-ethylenediamine (EDA) and/or diethylenetriamine (DETA) and/or PIP (from monoethanolamine (MEDA) and ammonia), 2-ethylhexylamine and bis(2-ethylhexyl)amine (from 2-ethylhexanol and $NH_3$), tridecylamine and bis(tridecyl)amine (from tridecanol and $NH_3$), n-octylamine (from n-octanol and $NH_3$), 1,2-propylenediamine (from 2-hydroxypropylamine and $NH_3$), 1-diethylamino-4-aminopentane (from 1-diethylamino-4-hydroxypentane and $NH_3$), N,N-di($C_{1-4}$-alkyl) cyclohexylamine (from cyclohexanone and/or cyclohexanol and di($C_{1-4}$-alkyl)amine), e.g. N,N-dimethyl-N-cyclohexylamine (DMCHA), polyisobutenamine (PIBA; with e.g. n~1000) (from polyisobutenaldehyde and $NH_3$), N—N-diisopropyl-N-ethylamine (Hünig base) (from N—N-diisopropylamine and acetaldehyde, N-methyl-N-isopropylamine (MMIPA) (from monomethylamine and acetone), n-propylamines (such as mono-/di-n-propylamine, N,N-dimethyl-N-n-propylamine (DMPA) (from propionaldehyde and/or n-propanol and $NH_3$ or DMA), N,N-dimethyl-N-isopropylamine (DMIPA) (from i-propanol and/or acetone and DMA), N,N-dimethyl-N-butylamines (1-butanol, 2-butanol or isobutanol and/or butanel, i-butanal or butanone and DMA), 2-(2-di($C_{1-4}$-alkyl)aminoethoxy)ethanol and/or bis(2-di($C_{1-4}$-alkyl)aminoethyl)ether (from DEG and di($C_{1-4}$-alkyl) amine), 1,2-ethylenediamine (EDA), monoethanolamine (MEOA), diethylenetriamine (DETA) and/or piperazine (PIP) (from monoethylene glycol (MEG) and ammonia), 1,8-diamino-3,6-dioxaoctane and/or 1-amino-8-hydroxy-3,6-dioxaoctane (from Methylene glycol (TEG) and ammonia), 1-methoxy-2-propylamine (1-methoxyisopropylamine, MOIPA) (from 1-methoxy-2-propanol and ammonia), N-cyclododecyl-2,6-dimethylmorpholine (dodemorph) (from cyclododecanone and/or cyclododecanol and 2,6-dimethylmorpholine), polyetheramine (from the corresponding polyether alcohol and ammonia). The polyether alcohols are, for example, polyethylene glycols or polypropylene glycols having a molecular weight in the range from 200 to 5000 g/mol, and the corresponding polyether amines are obtainable, for example, under the trade name PEA D230, D400, D2000, T403 or T5000 from BASF.

EXAMPLES

Example 1

Production of Amination Catalyst 1 (Based on Ni—Co—Cu/$ZrO_2$=Comparative Experiment According to EP-A-963 975)

An aqueous solution of nickel nitrate, cobalt nitrate, copper nitrate and zirconium acetate comprising 2.39% by weight of NiO, 2.39% by weight of CoO, 0.94% by weight of CuO and 2.82% by weight of $ZrO_2$ was precipitated simultaneously in a stirred vessel in a constant stream with a 20% strength aqueous sodium carbonate solution at a temperature of 70° C. in such a way that the pH of 7.0 measured by means of a glass electrode was maintained. The suspension obtained was filtered and the filter cake was washed with deionized water until the electrical conductivity of the filtrate was about 20 µS. The filter cake was then dried at a temperature of 150° C. in a drying oven or a spray dryer. The hydroxide/carbonate mixture obtained in this way was then heated at a temperature of from 450 to 500° C. for a period of 4 hours. The catalyst produced in this way had the composition: 28% by weight of NiO, 28% by weight of CoO, 11% by weight of CuO and 33% by weight of $ZrO_2$. The catalyst was mixed with 3% by weight of graphite and shaped to form pellets. The oxidic pellets were reduced. The reduction was carried out at 280° C., with the heating rate being 3° C./minute. Reduction was firstly carried out for 50 minutes using 10% of $H_2$ in $N_2$, subsequently for 20 minutes using 25% of $H_2$ in $N_2$, then for 10 minutes using 50% of $H_2$ in $N_2$, then for 10 minutes using 75% of $H_2$ in $N_2$ and finally for 3 hours using 100% $H_2$. The % ages quoted are in each case % by volume. The passivation of the reduced catalyst was carried out at room temperature in diluted air (air in $N_2$ having an $O_2$ content of not more than 5% by volume).

Example 2

The catalyst was produced in a manner analogous to catalyst 1. However, lead nitrate was additionally added to the nitrate solution. The catalyst 2 obtained in this way had the composition shown in table I.

Examples 3 and 4

The catalysts were produced in a manner analogous to catalyst 1. However, bismuth nitrate was additionally added to the nitrate solution. The catalysts 3 and 4 obtained in this way had the composition shown in table I.

Example 5

The catalyst was produced in a manner analogous to catalyst 1. However, indium nitrate was additionally added to the nitrate solution. The catalyst 5 obtained in this way had the composition shown in table I.

Examples 6 and 7

The catalysts were produced in a manner analogous to catalyst 1. However, tin dichloride was additionally added to the nitrate solution. The catalysts 6 and 7 obtained in this way had the composition shown in table I.

Example 8

Amination of Diethylene Glycol (DEG)

8 g of the reduced amination catalyst in the form of about 1 mm crushed material was placed in a 300 ml autoclave together with 80 g of diethylene glycol (0.75 mol). 34 g of liquid ammonia (2 mol) were added to the reaction mixture, the autoclave was pressurized to 70 bar by means of hydrogen and heated to 200° C. At 200° C., another 20 bar of hydrogen were injected, with the total pressure increasing to 180-200 bar. The autoclave was maintained at 200° C. for 12 hours while stirring.

Samples of the reaction mixture were taken at various points in time and analyzed by means of gas chromatography. The analysis was carried out using a 30 m long GC column "RTX-5 Amine" using a temperature program: 80° C./15 minutes, heating to 290° C. in 30 minutes, at 290° C./15 minutes.

The composition of the resulting reaction mixtures for the catalysts of examples 1 to 7 is shown in table I.

TABLE I

| | Catalyst | | | | | Performance | | | | | | Decarbonylation |
|---|---|---|---|---|---|---|---|---|---|---|---|---|
| | | | | | | | DEG | | | | | |
| # | Ni % | Co % | Cu % | Dop. | Dop. % | Time Hours | Conversion GC % | Mor GC % | ADG GC % | MeOEt GC % | MeOAE GC % | Decarbonyation Σ GC % | normalized** % |
| 1 | 21.9 | 21.9 | 10.5 | — | — | 4 | 64.3 | 31.0 | 21.7 | 0.40 | 0.15 | 0.60 | 0.94% |
| | | | | | | 8 | 83.8 | 53.6 | 12.6 | 0.30 | 0.31 | 0.73 | 0.87% |
| | | | | | | 12 | 94.9 | 69.6 | 4.5 | 0.19 | 0.40 | 0.82 | 0.86% |
| 2 | 22.7 | 21.3 | 10.3 | Pb | 1.2 | 8 | 51.2 | 16.8 | 28.2 | 0.11 | 0.04 | 0.22 | 0.43% |
| | | | | | | 10 | 68.1 | 25.5 | 31.9 | 0.11 | 0.05 | 0.23 | 0.34% |
| | | | | | | 12 | 86.3 | 46.2 | 22.3 | 0.10 | 0.09 | 0.28 | 0.33% |
| 3 | 19.1 | 18.9 | 9.1 | Bi | 6.8 | 8 | 48.4 | 14.3 | 25.3 | 0.06 | 0.02 | 0.11 | 0.23% |
| | | | | | | 10 | 60.0 | 20.7 | 26.3 | 0.07 | 0.03 | 0.15 | 0.24% |
| | | | | | | 12 | 63.4 | 18.9 | 26.6 | 0.06 | 0.03 | 0.13 | 0.20% |
| 4 | 22.0 | 21.5 | 10.5 | Bi | 0.6 | 8 | 49.2 | 10.1 | 32.5 | 0.05 | 0.01 | 0.11 | 0.23% |
| | | | | | | 10 | 67.4 | 20.9 | 34.6 | 0.06 | 0.03 | 0.17 | 0.25% |
| | | | | | | 12 | 81.2 | 32.8 | 29.6 | 0.06 | 0.05 | 0.30 | 0.37% |
| 5 | 22.0 | 21.5 | 10.2 | In | 1.6 | 8 | 82.0 | 41.7 | 22.8 | 0.07 | 0.05 | 0.18 | 0.22% |
| | | | | | | 10 | 85.2 | 48.3 | 19.2 | 0.07 | 0.06 | 0.26 | 0.30% |
| | | | | | | 12 | 95.9 | 69.3 | 6.7 | 0.06 | 0.10 | 0.37 | 0.39% |
| 6 | 22.7 | 21.3 | 11.0 | Sn | 0.2 | 4 | 51.7 | 23.8 | 20.7 | 0.12 | 0.08 | 0.28 | 0.54% |
| | | | | | | 8 | 93.9 | 62.3 | 7.1 | 0.08 | 0.15 | 0.35 | 0.37% |
| | | | | | | 12 | 95.0 | 65.0 | 5.6 | 0.07 | 0.17 | 0.40 | 0.42% |
| 7 | 22.7 | 22.4 | 10.8 | Sn | 0.4 | 8 | 65.6 | 35.1 | 11.4 | 0.05 | 0.10 | 0.29 | 0.44% |
| | | | | | | 10 | 88.8 | 53.7 | 9.1 | 0.05 | 0.14 | 0.39 | 0.44% |
| | | | | | | 12 | 91.1 | 54.0 | 7.9 | 0.05 | 0.13 | 0.38 | 0.42% |

*Catalyst composition in % by weight; balance to 100% is $ZrO_2$

**Sum of decarbonylation/DEG conversion

DEG diethylene glycol

Mor morpholine

ADG aminodiglycol

MeOEt methoxyethanol

MeOAE methoxyethylamine

Decarbonylation Sum of methanol, methoxyethanol, methoxyethylamine, N-methylmorpholine and methoxyethylmorpholine Work-Up:

The respective pure products could be obtained from the aqueous crude materials by rectification under reduced pressure, atmospheric pressure or superatmospheric pressure by known methods. The pure products are obtained here either directly in pure form or as an azeotrope with water. Water-comprising azeotropes can be dewatered by liquid-liquid extraction with concentrated sodium hydroxide solution before or after the purification by distillation. Dewatering by distillation in the presence of an entrainer in accordance with known methods is also possible.

If the crude material or the aliphatic amine in the crude material is barely miscible or immiscible with water, dewatering by separation of the organic phase and the aqueous phase using known methods is also possible.

The invention claimed is:

1. A catalytically active composition comprising, prior to reduction with hydrogen: 10 to 75% by weight of an oxygen compound of zirconium, calculated as $ZrO_2$; 1 to 30% by weight of an oxygen compound of copper, calculated as CuO; 10 to 50% by weight of an oxygen compound of nickel, calculated as NiO; 10 to 50% by weight of an oxygen compound of cobalt, calculated as CoO; and 0.1 to 10% by weight of one or more oxygen compounds of Sn, calculated as SnO.

2. The catalytically active composition according to claim 1, wherein the one or more oxygen compounds of Sn is present in an amount of 0.2 to 7% by weight, calculated as SnO.

3. The catalytically active composition according to claim 1, wherein the one or more oxygen compounds of Sn is present in an amount of 0.4 to 5% by weight, calculated as SnO.

4. The catalytically active composition according to claim 1, wherein the oxygen compound of zirconium is present in an amount of 25 to 65% by weight, calculated as $ZrO_2$; wherein the oxygen compound of copper is present in an amount of 2 to 25% by weight, calculated as CuO; wherein the oxygen compound of nickel is present in an amount of 13 to 40% by weight, calculated as NiO; and wherein the oxygen compound of cobalt is present in an amount of 13 to 40% by weight, calculated as CoO.

5. The catalytically active composition according to claim 1, wherein the oxygen compound of zirconium is present in an amount of 30 to 55% by weight, calculated as $ZrO_2$; wherein the oxygen compound of copper is present in an amount of 5 to 15% by weight, calculated as CuO; wherein the oxygen compound of nickel is present in an amount of 16 to 35% by weight, calculated as NiO; and wherein the oxygen compound of cobalt is present in an amount of 16 to 35% by weight, calculated as CoO.

6. The catalytically active composition according to claim 1, wherein nickel and copper are present in a molar ratio of nickel to copper of greater than 1.

* * * * *